United States Patent
Kitamura

(10) Patent No.: US 11,628,153 B2
(45) Date of Patent: Apr. 18, 2023

(54) AGENT FOR PREVENTING OR AMELIORITING NOCTURIA

(71) Applicant: Kao Corporation, Tokyo (JP)

(72) Inventor: Naoya Kitamura, Utsunomiya (JP)

(73) Assignee: Kao Corporation, Tokyo (JP)

( * ) Notice: Subject to any disclaimer, the term of this patent is extended or adjusted under 35 U.S.C. 154(b) by 296 days.

(21) Appl. No.: 16/975,184

(22) PCT Filed: May 27, 2019

(86) PCT No.: PCT/JP2019/020831
§ 371 (c)(1),
(2) Date: Aug. 24, 2020

(87) PCT Pub. No.: WO2019/230626
PCT Pub. Date: Dec. 5, 2019

(65) Prior Publication Data
US 2021/0077448 A1    Mar. 18, 2021

(30) Foreign Application Priority Data

May 28, 2018 (JP) .............................. JP2018-101411

(51) Int. Cl.
| | | |
|---|---|---|
| A61K 31/216 | (2006.01) | |
| A23L 33/105 | (2016.01) | |
| A61P 7/12 | (2006.01) | |
| A61P 13/00 | (2006.01) | |
| A23L 2/52 | (2006.01) | |
| A61K 9/00 | (2006.01) | |
| A61K 36/535 | (2006.01) | |

(52) U.S. Cl.
CPC .............. *A61K 31/216* (2013.01); *A23L 2/52* (2013.01); *A23L 33/105* (2016.08); *A61K 9/0056* (2013.01); *A61K 9/0095* (2013.01); *A61K 36/535* (2013.01); *A61P 7/12* (2018.01); *A61P 13/00* (2018.01); *A23V 2002/00* (2013.01)

(58) Field of Classification Search
CPC .................................................. A61K 31/216
See application file for complete search history.

(56) References Cited

U.S. PATENT DOCUMENTS

2010/0297230 A1   11/2010  Flectcher

FOREIGN PATENT DOCUMENTS

| CN | 101116727 A | 2/2008 |
|---|---|---|
| CN | 101422452 A | 5/2009 |
| CN | 102987036 A | 3/2013 |
| CN | 104800805 A | 7/2015 |
| CN | 107648307 A | 2/2018 |
| CN | 108030849 A | 5/2018 |
| JP | 2013-216592 A | 10/2013 |
| JP | 2013-216593 A | 10/2013 |
| JP | 2016-216364 A | 12/2016 |
| JP | 2017-052747 A | 3/2017 |
| WO | WO 2006/020994 A2 | 2/2006 |

OTHER PUBLICATIONS

Jiang et al. Basic & Clinical Pharmacology & Toxicology, 2012, 110: 390-395.*
Dani et al. Nat Rev Urol., 2016, 13(10): 573-83.*
International Search Report for PCT/JP2019/020831; I.A. fd May 27, 2019, dated Aug. 6, 2019 from the Japan Patent Office, Tokyo, Japan.
International Preliminary Report on Patentability (IPRP), Chapter I of the Patent Cooperation Treaty, including the Written Opinion, for PCT/JP2019/020831; I.A. fd May 27, 2019, dated Dec. 1, 2020, by the International Bureau of WIPO, Geneva, Switzerland.
Kwon, Yo et al., "Rosmarinic Acid Potentiates Pentobarbital-Induced Sleep Behaviors and Non-Rapid Eye Movement (NREM) Sleep through the Activation of $GABA_A$-ergic Systems," Biomol Ther (Seoul). Mar. 1, 2017;25(2):105-111. doi: 10.4062/biomolther. 2016.035. PMID: 27469144; PMCID: PMC5340534.
Kitamura N et al., "Perilla extract improves frequent urination in spontaneously hypertensive rats with enhancement of the urothelial presence and anti-inflammatory effects," Int J Urol. Mar. 2018;25(3):298-304. doi: 10.1111/iju.13516. Epub Dec. 21, 2017. PMID: 29268303.
Yokohama, T et al., "Effectiveness of Chinese herbal medicine, gosha-jinki-gan, for patients with overactive bladder," Journal of the West Japan Urological Assoc (Nishinihon J), 2006, 68:51-54.
Buser, N et al., Efficacy and adverse events of antimuscarinics for treating overactive bladder: network meta-analyses. Eur Urol. Dec. 2012;62(6):1040-60. doi: 10.1016/j.eururo.2012.08.060. Epub Sep. 7, 2012. PMID: 22999811.
Tavafi, M et al., Effect of rosmarinic acid on inhibition of gentamicin induced nephrotoxicity in rats. Tissue Cell. Dec. 2011;43(6):392-7. doi: 10.1016/j.tice.2011.09.001. Epub Oct. 13, 2011. PMID: 22000907.
Jiang WL et al., "Effect of rosmarinic acid on experimental diabetic nephropathy," Basic Clin Pharmacol Toxicol. Apr. 2012;110(4):390-5. doi: 10.1111/j.1742-7843.2011.00828.x. Epub Dec. 2, 2011. PMID: 22053730.
Extended European Search report including the supplementary European search report and the European search opinion, for EP Application No. 19811563.6, dated Jan. 28, 2022, European Patent Office, Munich, Germany.
Naber KG. Efficacy and safety of the phytotherapeutic drug Canephron® N in prevention and treatment of urogenital and gestational disease: review of clinical experience in Eastern Europe and Central Asia. Res Rep Urol. Feb. 4, 2013;5:39-46. doi: 10.2147/RRU.S39288. Erratum in: Res Rep Urol. 2013;5:81. PMTD: 24400233; PMCID: PMC3826901.
"Notification of the First Office Action," for CN Application No. 201980033294.9, mailing date Jan. 12, 2023, from the China National Intellectual Property Administration, Beijing, China.

* cited by examiner

*Primary Examiner* — Rei Tsang Shiao
(74) *Attorney, Agent, or Firm* — Sterne, Kessler, Goldstein & Fox P.L.L.C.

(57) ABSTRACT

An agent for preventing or ameliorating nocturia, containing rosmarinic acid or a salt thereof as an active ingredient.

19 Claims, No Drawings

AGENT FOR PREVENTING OR AMELIORITING NOCTURIA

TECHNICAL FIELD

The present invention relates to an agent for preventing or ameliorating nocturia, and a food or drink composition for preventing or ameliorating nocturia.

BACKGROUND ART

Frequent urination is a symptom with an increased daily urinary frequency due to various causes. The causes for frequent urination are largely divided into those involving an increase in urine volume, such as ones attributable to diabetes insipidus, hypertension, excessive intake of water, caffeine, and/or alcohol, or aging, and those independent of an increase in urine volume, such as ones attributable to overactive bladder, urinary tract infection, or interstitial bladder cystitis. Further, the presence of dysfunction in urinary system organs such as the bladder and prostate or of neurotonic reaction is known to cause frequent urination.

Among urination disorders, including frequent urination and the like, one that has attracted particular attention is nocturia. Nocturia is a symptom in which one has to wake up during the sleep to urinate. It is known that a considerable percentage of lower urinary tract symptoms suffers are accounted for by patients with nocturia symptoms. As nocturia makes high-quality sleep impossible, the afflicted person comes to have trouble with everyday life activities and therefore experiences a decline in quality of life. Nocturia often intensifies with aging. The number of Japanese patients aged over 40 are estimated to exceed 45 million. Nocturia has therefore attracted attention as an affliction associated with today's aging society.

Nocturia is triggered by various conditions, such as overproduction of urine at night and decreased bladder capacity, and is thought to develop in association with many factors. Once nocturia develops, sound sleep may be disrupted because desire to urinate and/or feeling of abdominal tension during sleep make the person apprehensive about urination. However, nocturia is thought to be prompted by causes different from frequent urination when not sleeping (also called "daytime frequent urination"), but the onset mechanism remains largely unknown.

Herbal medicines effective in preventing or ameliorating overactive bladder have been reported in, for instance, Journal of The WEST Japan Urological Association, 2006, Vol. 68, p. 51-54. Although the herbal medicines discussed in the Journal of The WEST Japan Urological Association, 2006, Vol. 68, p. 51-54 is effective in preventing or ameliorating urinary urgency and/or daytime frequent urination, it is reported not to decrease urinary frequency during sleep.

Regarding treatment of lower urinary tract symptoms using a drug, an anticholinergic agent that inhibits bladder contraction promoting action of acetylcholine is reported to be effective. EUROPEAN UROLOGY, 2012, Vol. 62, p. 1040-1060 reports that intake of an anticholinergic agent ameliorates daytime urination, one of the symptoms of overactive bladder, but does not exert satisfactory effect on nocturia. In addition, intake of an anticholinergic agent is known to cause adverse effects such as thirst, constipation, and urination difficulties. Further, an anticholinergic agent inhibits binding of released acetylcholine to its receptor on bladder smooth muscle, in what is called symptomatic treatment. For these reasons, intake of an anticholinergic agent cannot be said to be a potent protocol for treatment of nocturia from the viewpoint of efficacy.

In view of such circumstances, a safer and more effective agent for preventing or ameliorating nocturia is desired.

Rosmarinic acid has been reported to be effective in preventing or ameliorating, inter alia, vesicoureteral reflux, urinary incontinence, and renal impairment (see JP-A-2017-52747 ("JP-A" means unexamined published Japanese patent application), WO 2006/020994, Tissue Cell, 2011, vol. 43, p. 392-397, and Basic & Clinical Pharmacology & Toxicology, 2012, vol. 110, p. 390-395).

However, intake of rosmarinic acid is not known to be effective in preventing or ameliorating nocturia.

SUMMARY OF INVENTION

The present invention relates to an agent for preventing or ameliorating nocturia, containing rosmarinic acid or a salt thereof as an active ingredient.

Further, the present invention relates to a food or drink composition for preventing or ameliorating nocturia, containing rosmarinic acid or a salt thereof as an active ingredient.

Other and further features and advantages of the invention will appear more fully from the following description.

MODE FOR CARRYING OUT THE INVENTION

The present invention relates to an agent for preventing or ameliorating nocturia and a food or drink composition for preventing or ameliorating nocturia, which are effective for decreasing frequency of waking up due to urination during sleep.

In addition, the present invention relates to an agent for preventing or ameliorating nocturia and a food or drink composition for preventing or ameliorating nocturia, which are effective for decreasing urinary desire during sleep, mitigating feeling of abdominal tension, and supporting sound sleep.

Further, the present invention relates to an agent for preventing or ameliorating nocturia and a food or drink composition for preventing or ameliorating nocturia, which are effective for reducing apprehension about urination during sleep.

The present inventor has conducted intensive research on substances capable of preventing or ameliorating nocturia. As a result, it was found that rosmarinic acid has an action of preventing or ameliorating nocturia, and is useful for preventing or ameliorating nocturia.

The present invention was completed based on these findings.

The agent for preventing or ameliorating nocturia and the food or drink composition for preventing or ameliorating nocturia according to the present invention can prevent or ameliorate nocturia and decrease the frequency of waking up due to urination during sleep. In addition, the agent for preventing or ameliorating nocturia and the food or drink composition for preventing or ameliorating nocturia according to the present invention can decrease a urinary desire during sleep, mitigate a feeling of abdominal tension, and support sound sleep. Besides, administration or intake of the agent for preventing or ameliorating nocturia or the food or drink composition for preventing or ameliorating nocturia according to the present invention can reduce apprehension about urination during sleep.

The term "prevention" as used herein means the prevention or delay of the onset of disease or symptom in individual bodies, or reduction in the risk of the onset of disease or symptom in individual bodies.

Further, the term "amelioration" as used herein means an improvement of disease, symptom or condition, prevention or delay of aggravation of disease, symptom or condition, or reverse, prevention or delay of the progress of disease, symptom or condition.

In the present specification, "nocturia" refers to a symptom that requires waking up to urinate during sleep. Waking up one or more times during sleep to urinate is usually defined as nocturia.

Note that the "nocturia" is clearly distinct from "daytime (diurnal) frequent urination". Examples of the rationale include that nocturia occurs as an anti-diuretic hormone, secretion of which is usually increased during night, decreases with aging. Further, the bladder capacity is usually larger during night than during daytime, but the bladder capacity during night decreases as the circadian rhythm is disturbed more due to, for instance, shift work. This is also one of the causes.

Meanwhile, as used herein, the term "during night" means the same as during sleep. The term "during daytime" refers to a period other than during sleep. That is, as used herein, the terms "during night" and "during daytime" are not used to represent a temporal meaning, but are used to represent one of the time during sleep or the other time zone.

The agent for preventing or ameliorating nocturia of the present invention (hereinafter, also referred to as "preventing or ameliorating agent of the present invention") contains rosmarinic acid or a salt thereof as an active ingredient. Further, the food or drink composition for preventing or ameliorating nocturia of the present invention (hereinafter, also simply referred to as "food or drink composition") contains rosmarinic acid or a salt thereof as an active ingredient.

The salt is not particularly limited if the salt is pharmaceutically acceptable. Examples include: alkali metal salts such as a sodium salt and a potassium salt; alkali earth metal salts such as a calcium salt and a magnesium salt; and amine salts such as an ammonium salt and a triethylamine salt. In the present invention, the salt is preferably at least one kind of salt selected from the group consisting of alkali metal salts and alkali earth metal salts, more preferably at least one kind of salt selected from the group consisting of a sodium salt and a calcium salt, and further preferably a sodium salt.

There is no particular limitation in a method of producing rosmarinic acid or a salt thereof, which can be prepared by ordinarily organic chemical synthesis. Alternatively, it may be obtained by extraction and/or purification from naturally occurring material. In addition, commercially available reagents may be used.

Rosmarinic acid or a salt thereof can be produced by suspension culture of Lamiaceae family plant cells with reference to, for instance, the procedure described in JP-B-1-29558 ("JP-B" means examined Japanese patent publication).

Further, in the present invention, it is possible to use, as an active ingredient rosmarinic acid or a salt thereof, an extract containing rosmarinic acid or a salt thereof that is extracted from a natural product containing rosmarinic acid or a salt thereof. Examples of the natural product containing rosmarinic acid or a salt thereof include plants belonging to the Lamiaceae family. Specifically, at least one kind of plant selected from the group consisting of *Perilla frutescens* Britton var. *acuta* Kudo, *Perilla frutescens* var. *crispa* f. *viridis*. Makino, *Rosmarinus officinalis*, *Melissa officinalis*, *Salvia officinalis* and *Orthosiphon aristatus* is preferably used. Among these, it is preferable to use an extract of *Perilla frutescens* Britton var. *acuta* Kudo containing rosmarinic acid or a salt thereof in the present invention.

To obtain a Lamiaceae family plant extract containing rosmarinic acid or a salt thereof, an ordinarily method may be used to carry out extraction from at least one kind selected from the group consisting of the whole plant, leaves, stems, roots, and seeds of the above Lamiaceae family plant and preferably from leaves of the Lamiaceae family plant.

As the extraction method, a solvent extraction method using a water-soluble solvent is preferable. Examples of the water-soluble solvent include water, a water-soluble organic solvent, or a mixed solvent thereof. Examples of the water-soluble organic solvent include monovalent alcohols having 1 to 5 carbon atoms such as ethanol and butanol; and polyvalent alcohols such as ethylene glycol, polypropylene glycol, 1,3-butyrene glycol and 1,4-butyrene glycol. Of these, water, ethanol or ethanol aqueous solution is preferably used. In addition, the extraction conditions may be at room temperature or at a high temperature. Also, the extraction may be carried out at ordinary pressure, or the extraction may be carried out under pressurized conditions. Further, the extraction may be carried out while left to stand, or the extraction may be carried out while mixing.

Furthermore, to increase the content of rosmarinic acid or a salt thereof, the resulting extract may be subject to, if appropriate, fractionation and purification using a known procedure. Specifically, one can consult the methods described in European Journal of Nutrition, 2005, vol. 44, p. 1-9 and Planta medics, 2016, vol. 82, p. 388-406.

Moreover, some commercially available extracts containing rosmarinic acid or a salt thereof may be used. Examples of the extract of *Perilla frutescens* Britton var. *acuta* Kudo include trade name: "NICHINO AkashisoEkisu" RA15P (manufactured by NICHINOKAGAKU, Co., Ltd.). Examples of the extract of *Perilla frutescens* var. *crispa* f. *viridis*. Makino include trade name: "ShisoEkisu" OGI (manufactured by Ogawa & Co., Ltd.). Examples of the extract of *Rosmarinus officinalis* include trade name: "Rosemary Ekisu" MF (manufactured by MARUZEN PHARMACEUTICALS CO., LTD.). Examples of the extract of *Melissa officinalis* include trade name: "Lemon Balm Ekisu Powder" MF (manufactured by MARUZEN PHARMACEUTICALS CO., LTD.). Examples of the extract of *Salvia officinalis* include trade name: *Salvia*-Sage (Finzelberg, Inc.). Examples of the extract of *Orthosiphon aristatus* extract include trade name: "Kumisukutin Ekisu Matu" (manufactured by KANEHIDE BIO CO., LTD.).

Lamiaceae family plants, such as *Perilla frutescens* Britton var. *acuta* Kudo, *Perilla frutescens* var. *crispa* f. *viridis*. Makino, *Rosmarinus officinalis*, *Melissa officinalis*, *Salvia officinalis*, and *Orthosiphon aristatus*, have conventionally been used as foods. Thus, use of an extract from each Lamiaceae family plant as an active ingredient rosmarinic acid or a salt thereof according to the present invention makes it possible to provide a highly safe agent and food or drink composition for preventing or ameliorating nocturia.

In the case of using an extract from the Lamiaceae family plant, the ratio of rosmarinic acid or a salt thereof occupied in the extract with respect to the extract solid content in terms of rosmarinic acid content is preferably 0.1 mass % or more, more preferably 1 mass % or more, and further preferably 10 mass % or more. The upper limit is 100 mass %, preferably 95 mass % or less, and more preferably 90 mass % or less. Alternatively, the percentage is preferably from 0.1 mass % to 100 mass %, more preferably from 1 mass % to 95 mass %, and further preferably from 10 mass % to 90 mass %. Note that as used herein, the "extract solid content" refers to the residue prepared by drying the extract using a dryer at 105° C. for 3 hours so as to remove a volatile substance.

As demonstrated in Examples below, administration or intake of rosmarinic acid is not found to be able to ameliorate daytime frequent urination. By contrast, administration or intake of rosmarinic acid can significantly decrease the urinary frequency during sleep (during night). Thus, rosmarinic acid or a salt thereof can be used to prevent or ameliorate nocturia. Further, prevention or amelioration of nocturia allows for a decrease in urinary desire or mitigation of feeling of abdominal tension during sleep, thereby capable of supporting sound sleep. The feeling of abdominal tension herein means a restless feeling and/or an unsettled feeling, where one wants to go to rest room during daily living. Also, apprehension about urination during sleep can be reduced.

The above use may involve therapeutic use (i.e., medical practice) or non-therapeutic use (non-medical practice). In addition, a subject for the above use may be a human or a non-human animal, or may be a sample therefrom. The term "non-therapeutic" as used herein is a concept excluding a medical action, that is, treatment action on human bodies by therapy.

The preventing or ameliorating agent of the present invention is a specific embodiment of the above use and is applicable to any of therapeutic application (medical application) or non-therapeutic application (non-medical application). Specifically, the agent can be used as, for instance, a pharmaceutical product or a quasi-drug. In addition, the preventing or ameliorating agent of the present invention can be blended in, for instance, various kinds of food or drink, feed, or pet food.

The preventing or ameliorating agent of the present invention may be used as various dosage forms applicable to humans or non-human animals (preferably mammals), such as liquids, solids, emulsions, pastes, gels, powder (powdery forms), granules, pellets, or sticks.

The preventing or ameliorating agent of the present invention may consist of the above compound as an active ingredient or may include an additional component(s) without affecting the efficacy. Examples of the additional component(s) include the following additives.

When the preventing or ameliorating agent of the present invention is applied as a pharmaceutical product or a quasi-drug, an effective amount of the compound may be included and optionally blended with an additive(s) to prepare the agent in various dosage forms. For instance, the agent may be prepared as an oral medicine such as a tablet, a coated tablet, a capsule, granules, powder, a syrup, an enteric agent, a troche, or a drink; or the agent may be prepared as a parenteral medicine such as an injection, a suppository, a transdermal agent, or an external preparation. In this way, each pharmaceutical product or quasi-drug may be prepared. Among the forms, the oral medicine is a preferable form.

To prepare the pharmaceutical product or quasi-drug in various dosage forms, additives may be used for preparation in accordance with an ordinarily protocol. Ordinarily used additives may be utilized. Examples of the additive(s) include pharmaceutically acceptable excipients, liquid carriers, oil carriers, stabilizers, wetting agents, emulsifiers, binders, isotonic agents, disintegrating agents, lubricants, bulking agents, surfactants, dispersing agents, suspending agents, diluents, osmotic pressure modifiers, pH modifiers, antiseptics, antioxidants, colorants, UV absorbers, moisturizers, thickeners, brighteners, buffers, preservatives, flavoring agents, fragrances, coating agents, odorants, and/or antimicrobials.

In the case where the preventing or ameliorating agent of the present invention or the above-described active ingredient may be applied to or blended with, for instance, food or drink, feed, or pet food to produce a food or drink composition, a feed composition, a pet food composition or the like, the composition may be provided, by molding, as a form fit for food or drink, such as granules, grains, liquids, gels, tablets, capsules, or pastes. Further, the food or drink composition may have a form of general foods or drinks as well as a form of those that have a concept of preventing or ameliorating nocturia and are optionally labeled with the idea, including functional foods and drinks such as beauty foods, sick foods, nutritionally functional foods, foods for specified health use, or functional foods.

Examples of a food or drink product blended therewith include processed flour foods, processed rice foods, confectioneries, beverages, dairy products, seasonings, processed meat storage foods, processed seafoods, or cooking oils. In addition, the above food or drink composition may have a form of, for instance, oral enteral nutritional foods such as tablet foods such as tablets or capsules, concentrated liquid foods, natural liquid foods, semi-digestive nutritional supplements, component nutritional supplements, or drink nutritional supplements.

Examples of the feed composition or the pet food composition include feeds for small animals such as rabbits, rats, or mice, or pet foods for dogs, cats, or squirrels.

For instance, these food or drink composition, feed composition, and pet food composition contain the preventing or ameliorating agent of the present invention or the above-described active ingredient, and may be prepared, in accordance with an ordinarily protocol, while blended, if appropriate, with food raw material(s) such as additives such as a sweetener, a coloring agent, an anti-oxidant, vitamins, a fragrance, and/or a mineral, proteins, lipids, sugars, carbohydrates, and/or food fibers.

The blending amount or the content of the above active ingredient in the preventing or ameliorating agent or the food or drink composition according to the present invention may be determined, if appropriate, depending on their usage.

For instance, in the case of oral solid preparations such as tablets, coated tablets, granules, powders, capsules, or oral liquid preparations such as oral solutions and syrups, the blending amount or the content of the active ingredient with respect to the total amount of the preventing or ameliorating agent or the food or drink composition according to the present invention in terms of rosmarinic acid content is preferably 0.01 mass % or more, more preferably 0.1 mass % or more, and further preferably 1 mass % or more and preferably 100 mass % or less, 90 mass % or less, and further preferably 70 mass % or less. Alternatively, it is preferably 0.01 to 100 mass %, more preferably 0.1 to 90 mass %, and further preferably 1 to 70 mass %.

When the preventing or ameliorating agent of the present invention is blended with, for instance, a food or drink product or a pet food, the blending amount or the content of the above active ingredient with respect to the total amount of the preventing or ameliorating agent or the food or drink composition according to the present invention in terms of rosmarinic acid content is preferably 0.001 mass % or more, more preferably 0.01 mass % or more, and further preferably 0.1 mass % or more and preferably 50 mass % or less, more preferably 10 mass % or less, and further preferably 3 mass % or less. Alternatively, it is preferably 0.001 to 50 mass %, more preferably 0.01 to 10 mass %, and further preferably 0.1 to 3 mass %.

The amount of administration or intake of the preventing or ameliorating agent of the present invention and the food or drink composition can be appropriately determined according to a state of an individual, a body weight thereof, a sex thereof, an age thereof, or other factors. For example, the amount of administration or intake of the compound in terms of rosmarinic acid content for one (1) adult (body weight 60 kg) per one (1) day is preferably 0.1 mg or more, more preferably 10 mg or more, and further preferably 50 mg or more, and preferably 40,000 mg or less, more preferably 15,000 mg or less, and further preferably 5,000 mg or less. Alternatively, the amount is preferably 0.1 to 40,000 mg, more preferably 10 to 15,000 mg, and further preferably 50 to 5,000 mg.

The preventing or ameliorating agent and the food or drink composition of the present invention can be ingested or administered once a day or divisionally several times a day or during an arbitrary period and at intervals. The period of ingestion or administration of the compound can be determined properly, and the period is preferably, for example, one (1) day or more, more preferably seven (7) days or more, and further preferably thirty (30) days or more.

Subjects for ingestion or administration of the above pharmaceutical product, quasi-drug, or food or drink composition are not particularly limited and are preferably humans or non-human mammals who want or need prevention, amelioration, or treatment of nocturia. Note that examples of the subjects for ingestion or administration include humans and non-human mammals with a manifested nocturia symptom, humans and non-human mammals at a risk thereof, and humans and non-human mammals in which such a disease or symptom should be prevented. Examples of a specific nocturia symptom in humans include the cases where the frequency of waking up for urination one or more times during sleep is, in a weekly average, one (1) day or more, preferably two (2) days or more, more preferably three (3) days or more, and further preferably four (4) days or more.

The age of the subject to which the preventing or ameliorating agent and the food or drink composition of the present invention is ingested or administered is preferably 20 years old or older, more preferably 40 years old or older, further preferably 60 years old or older.

With regard to the embodiments described above, the present invention also discloses preventing or ameliorating agents, food or drink compositions, and methods, described below.

<1> An agent for preventing or ameliorating nocturia, containing rosmarinic acid or a salt thereof as an active ingredient.

<2> A food or drink composition for preventing or ameliorating nocturia, containing rosmarinic acid or a salt thereof as an active ingredient.

<3> The agent or composition described in the above item <1> or <2>, wherein the rosmarinic acid or the salt thereof is an extract of a plant belonging to the Lamiaceae family containing rosmarinic acid or a salt thereof; preferably an extract of at least one kind of plant selected from the group consisting of *Perilla frutescens* Britton var. *acuta* Kudo, *Perilla frutescens* var. *crispa* f. *viridis*. Makino, *Rosmarinus officinalis, Melissa officinalis, Salvia officinalis* and *Orthosiphon aristatus* containing rosmarinic acid or a salt thereof; and more preferably an extract of *Perilla frutescens* Britton var. *acuta* Kudo containing rosmarinic acid or a salt thereof.

<4> The agent or composition described in the above item <3>, wherein the ratio of rosmarinic acid or a salt thereof occupied in the extract of the plant belonging to the Lamiaceae family with respect to the extract solid content in terms of rosmarinic acid content is 0.1 mass % or more, preferably 1 mass % or more, and more preferably 10 mass % or more; and 100 mass % or less, preferably 95 mass % or less, and more preferably 90 mass % or less.

<5> The agent or the composition as described in any one of the above items <1> to <4>, wherein the blending amount or the content of the active ingredient in terms of rosmarinic acid content is 0.01 mass % or more, preferably 0.1 mass % or more, more preferably 1 mass % or more, and 100 mass % or less, preferably 90 mass % or less, more preferably 70 mass % or less, in the total amount of the agent or the food or drink composition.

<6> The agent or the composition as described in any one of the above items <1> to <4>, wherein the blending amount or the content of the active ingredient in terms of rosmarinic acid content is 0.001 mass % or more, preferably 0.01 mass % or more, more preferably 0.1 mass % or more, and 50 mass % or less, preferably mass % or less, more preferably 3 mass % or less, in the total amount of the agent or the food or drink composition.

<7> Use of rosmarinic acid or a salt thereof, as an agent for preventing or ameliorating nocturia or a food or drink composition for preventing or ameliorating nocturia.

<8> Use of rosmarinic acid or a salt thereof, for producing an agent for preventing or ameliorating nocturia or a food or drink composition for preventing or ameliorating nocturia.

<9> A method of using rosmarinic acid or a salt thereof, as an agent for preventing or ameliorating nocturia or a food or drink composition for preventing or ameliorating nocturia.

<10> A method of preventing or ameliorating nocturia, containing administering or ingesting rosmarinic acid or a salt thereof.

<11> The use or method described in any one of the above items <7> to <10>, wherein the rosmarinic acid or the salt thereof is an extract of a plant belonging to the Lamiaceae family containing rosmarinic acid or a salt thereof; preferably an extract of at least one kind of plant selected from the group consisting of *Perilla frutescens* Britton var. *acuta* Kudo, *Perilla frutescens* var. *crispa* f. *viridis*. Makino, *Rosmarinus officinalis, Melissa officinalis, Salvia officinalis* and *Orthosiphon aristatus* containing rosmarinic acid or a salt thereof; and more preferably an extract of *Perilla frutescens* Britton var. *acuta* Kudo containing rosmarinic acid or a salt thereof.

<12> The use or method described in the above item <11>, wherein the ratio of rosmarinic acid or a salt thereof occupied in the extract of the plant belonging to the Lamiaceae family with respect to the extract solid content in terms of rosmarinic acid content is 0.1 mass % or more, preferably 1 mass % or more, and more preferably 10 mass % or more; and 100 mass % or less, preferably 95 mass % or less, and more preferably 90 mass % or less.

<13> The use or method described in any one of the above items <7> and <9> to <12>, wherein the compound is used for a subject who wants or needs prevention, amelioration, or treatment of nocturia and preferably a human in which frequency of waking up for urination one or more times during sleep is, in a weekly average, one (1) day or more, preferable two (2) days or more, more preferably three (3) days or more, and further preferably four (4) days or more.

<14> The use or method described in the above item <13>, wherein the age of the subject to which the compound is applied is preferably 20 years old or older, more preferably 40 years old or older, further preferably 60 years old or older.

<15> The use or method described in any one of the above items <7> and <9> to <14>, wherein the amount of administration or intake of the compound in terms of rosmarinic acid content for one (1) adult (body weight 60 kg) per one (1) day is 0.1 mg or more, preferably 10 mg or more, more preferably 50 mg or more, and 40,000 mg or less, preferably 15,000 mg or less, more preferably 5,000 mg or less.

<16> The use or method described in any one of the above items <7> to <9> and <11> to <15>, wherein the blending amount or the content of the compound in terms of rosmarinic acid content is 0.01 mass % or more, preferably 0.1 mass % or more, more preferably 1 mass % or more, and 100 mass % or less, preferably 90 mass % or less, more preferably 70 mass % or less, in the total amount of the agent or the food or drink composition.

<17> The use or method described in any one of the above items <7> to <9> and <11> to <15>, wherein the blending amount or the content of the compound in terms of rosmarinic acid content is 0.001 mass % or more, preferably 0.01 mass % or more, more preferably 0.1 mass % or more, and 50 mass % or less, preferably 10 mass % or less, more preferably 3 mass % or less, in the total amount of the agent or the food or drink composition.

<18> The use or method described in any one of the above items <7> and <9> to <17>, wherein the compound can be ingested or administered once a day or divisionally several times a day or during an arbitrary period and at intervals.

<19> The use or method described in any one of the above items <7> and <9> to <18>, wherein the period of ingestion or administration of the compound is one (1) day or more, preferably seven (7) days or more, more preferably thirty (30) days or more.

<20> Rosmarinic acid or a salt thereof for use in a method of preventing or ameliorating nocturia.

<21> Use of rosmarinic acid or a salt thereof, for manufacture of a drug for preventing or ameliorating nocturia.

<22> The compound or use described in the above item <20> or <21>, wherein the rosmarinic acid or the salt thereof is an extract of a plant belonging to the Lamiaceae family containing rosmarinic acid or a salt thereof; preferably an extract of at least one kind of plant selected from the group consisting of *Perilla frutescens* Britton var. *acuta* Kudo, *Perilla frutescens* var. *crispa* f. *viridis*. Makino, *Rosmarinus officinalis*, *Melissa officinalis*, *Salvia officinalis* and *Orthosiphon aristatus* containing rosmarinic acid or a salt thereof; and more preferably an extract of *Perilla frutescens* Britton var. *acuta* Kudo containing rosmarinic acid or a salt thereof.

<23> The compound or use described in the above item <22>, wherein the ratio of rosmarinic acid or a salt thereof occupied in the extract of the plant belonging to the Lamiaceae family with respect to the extract solid content in terms of rosmarinic acid content is 0.1 mass % or more, preferably 1 mass % or more, and more preferably 10 mass % or more; and 100 mass % or less, preferably 95 mass % or less, and more preferably 90 mass % or less.

<24> The compound or use described in any one of the above items <20> to <23>, wherein the compound is applied in the form of a pharmaceutical composition.

<25> The compound or use described in any one of the above items <20> to <23>, wherein the compound is applied in the form of a food or drink.

<26> The compound or use described in the above item <25>, wherein the form of a food or drink is sick foods, nutritionally functional foods, foods for specified health use, or functional foods.

<27> The compound or use described in any one of the above items <20> to <26>, wherein the compound is applied for a subject who wants or needs prevention, amelioration, or treatment of nocturia and preferably a human in which frequency of waking up for urination one or more times during sleep is, in a weekly average, one (1) day or more, preferable two (2) days or more, more preferably three (3) days or more, and further preferably four (4) days or more.

<28> The compound or use described in the above item <27>, wherein the age of the subject to which the compound is applied is preferably 20 years old or older, more preferably 40 years old or older, further preferably 60 years old or older.

<29> The compound or use described in any one of the above items <20> to <28>, wherein the amount of administration or intake of the compound in terms of rosmarinic acid content for one (1) adult (body weight 60 kg) per one (1) day is 0.1 mg or more, preferably 10 mg or more, more preferably 50 mg or more, and 40,000 mg or less, preferably 15,000 mg or less, more preferably 5,000 mg or less.

<30> The compound or use described in any one of the above items <20> to <29>, wherein the blending amount or the content of the compound in terms of rosmarinic acid content is 0.01 mass % or more, preferably 0.1 mass % or more, more preferably 1 mass % or more, and 100 mass % or less, preferably 90 mass % or less, more preferably 70 mass % or less.

<31> The compound or use described in any one of the above items <20> to <29>, wherein the blending amount or the content of the compound in terms of rosmarinic acid content is 0.001 mass % or more, preferably 0.01 mass % or more, more preferably 0.1 mass % or more, and 50 mass % or less, preferably 10 mass % or less, more preferably 3 mass % or less.

<32> The compound or use described in any one of the above items <20> and <22> to <31>, wherein the compound can be ingested or administered once a day or divisionally several times a day or during an arbitrary period and at intervals.

<33> The compound or use described in any one of the above items <20> and <22> to <32>, wherein the period of ingestion or administration of the compound is one (1) day or more, preferably seven (7) days or more, more preferably thirty (30) days or more.

<34> The agent, composition, use, method or compound described in any one of the above items <1> to <33>, wherein the nocturia is a symptom of having to wake up for urination during sleep.

<35> The agent, composition, use, method or compound described in any one of the above items <1> to <34>, wherein the nocturia is a case of waking up for urination one or more times during sleep.

<36> The agent, composition, use, method or compound described in any one of the above items <1> to <35>, wherein prevention or amelioration of the nocturia decreases a urinary desire or a feeling of abdominal tension during sleep and supports sound sleep.

<37> The agent, composition, use, method or compound described in any one of the above items <1> to <36>, wherein prevention or amelioration of the nocturia reduces apprehension about urination during sleep.

<38> The agent, composition, use, method or compound described in any one of the above items <1> to <37>, wherein the salt is at least one kind of salt selected from the group consisting of alkali metal salts and alkali earth metal salts, preferably at least one kind of salt selected from the group consisting of a sodium salt and a calcium salt, and more preferably a sodium salt.

EXAMPLES

Hereinafter, the present invention will be described more in detail with reference to Examples, but the present invention is not limited thereto.

Test Example 1: How Oral Intake of Rosmarinic Acid Affected Urination Function in Rats For the test, Spontaneously Hypertensive Rats (SHRs, see American Journal of Physiology, 1998, vol. 275, p. R1279-1286 and Neurourology and Urodynamics, 2005, vol. 24, p. 295-300) (42-week-old, female, obtained from Japan SLC) were used.

SHRs in the treatment group (n=12) ingested, for 8 weeks, a rosmarinic acid-containing feed (composition: 0.5 mass % rosmarinic acid (obtained from Carbosynth, Inc.), 66 mass % starch, 20 mass % casein, 5 mass % corn oil, 4 mass % cellulose, 3.5 mass % mineral, and 1 mass % vitamin). SHRs in the control group (n=12) ingested, for 8 weeks, a rosmarinic acid-free feed (composition: 66.5 mass % starch, 20 mass % casein, 5 mass % corn oil, 4 mass % cellulose, 3.5 mass % mineral, and 1 mass % vitamin). Then, their urination behavior was recorded in metabolic cages. Note that, before the recording in the metabolic cages, 4-day adaptation period was provided, and they were reared individually.

The urination behavior recording (measurement of the urinary frequency and the urine volume) was carried out under conditions with free access to feed and water and under conditions with a 12/12-h light/dark cycle. The urine volume was weighed with an electronic balance while the urine was collected every urination. Note that a past report (see Neurourology and Urodynamics, 2017, vol. 36, p. 1034-1038) was consulted; the start time of a light period corresponding to a rest period of each rat was set to ZT0; the light period was divided into two periods of ZT0-6 and ZT6-12; and the urinary frequency during each period was defined as an indicator for nocturia. In addition, a dark period corresponding to an activity period was divided into two periods of ZT12-18 and ZT18-24; and the urinary frequency during each period was defined as an indicator for daytime frequent urination.

Table 1 shows the urinary frequencies and Table 2 shows the urine volumes after intake of the test feed while data on the rest period and the activity period was tabulated every 6 hours. The results were means±standard errors. To compare the inter-group means, Student-t test was used.

TABLE 1

<Mean urinary frequency (times/6 h) of rats during rest period and activity period>

| | Rest period | | Activity period | |
| --- | --- | --- | --- | --- |
| | ZT0-6 | ZT6-12 | ZT12-18 | ZT18-24 |
| Control group | 2.7 ± 0.1 | 3.3 ± 0.3 | 6.2 ± 0.9 | 5.9 ± 0.7 |
| Treatment group | 2.5 ± 0.2 | 2.4 ± 0.2 | 6.7 ± 1.1 | 6.0 ± 0.7 |
| Significant difference | N.S. | P <0.05 | N.S. | N.S. |

TABLE 2

<Mean urine volume (mL/6 h) of rats during rest period and activity period>

| | Rest period | | Activity period | |
| --- | --- | --- | --- | --- |
| | ZT0-6 | ZT6-12 | ZT12-18 | ZT18-24 |
| Control group | 1.8 ± 0.1 | 1.4 ± 0.1 | 2.2 ± 0.3 | 2.4 ± 0.3 |
| Treatment group | 1.7 ± 0.1 | 1.1 ± 0.1 | 2.4 ± 0.4 | 2.4 ± 0.2 |
| Significant difference | N.S. | N.S. | N.S. | N.S. |

As shown in Table 1, the mean urinary frequency during the rest period (ZT6-12) corresponding to a sleeping period in rats was significantly less in the treatment group than in the control group.

By contrast, as show in Table 2, any significant difference in the mean urine volume during each time zone was undetected.

Test Example 2: How Oral Intake of Rosmarinic Acid-Containing *Perilla* Extract Affected Urination Function in Humans (1) Subjects Fourteen healthy males in the twenties to the fifties.

The average age of the subjects at the start of this study was 38.6±2.8 years old and the average BMI was 21.8±0.6. In addition, the mean urinary frequency during daytime (other than during sleep) at the start of this study was 7.6±0.4 times and the mean urinary frequency during night (during sleep) was 0.24±0.11 times.

(2) Preparation of Investigational Product

A commercially available *Perilla frutescens* Britton var. *acuta* Kudo water extract (trade name: "NICHINO Akashi-soEkisu" RA15P; manufactured by NICHINOKAGAKU, Co., Ltd.; containing rosmarinic acid in an amount of 15,400 mg/100 g) was filled into No. 2 capsules (trade name: gelatin capsule, manufactured by Qualicaps Co., Ltd.) at a rosmarinic acid content of 25 mg per capsule to prepare capsules encapsulating a rosmarinic acid-containing *Perilla* extract. Also prepared were rosmarinic acid-free placebo capsules into which instead of the rosmarinic acid-containing *Perilla* extract, an equivalent amount of starch was filled.

(3) Study Design

Two-group crossover study (washout period: 28 days or longer)

(i) Treatment group (capsules encapsulating the rosmarinic acid-containing *Perilla* extract; 4 capsules/day; containing 100 mg rosmarinic acid)

(ii) Control group (rosmarinic acid-free placebo capsules; 4 capsules/day)

(4) How to Intake Capsule

The respective capsules (2 capsules) were ingested with 100 mL of mineral water twice daily (within 30 min after breakfast and after dinner) for 28 days.

(5) How to Evaluate Frequent Urination

The situation of urination before and after the intake of capsules was recorded for 3 days, and the urinary frequencies (during daytime and during night) and the daily urine volume, for instance, were recorded.

Note that during this study period, the study was conducted while attention was paid to the following points.

(Important Points)

(i) Beverages other than non-caffeine tee beverage and water were not drunk, and intake of caffeine was prohibited.

(ii) Intake of *Perilla*-containing food was prohibited.

(iii) Vigorous exercise with sweating was prohibited.

(iv) Go to bed in a normal way (at 2 hours before or after their average bedtime).
(v) Slept under the same sleep environment as usual (lighting, temperature and humidity settings, the opening/closing of window).

(6) Statistical Test

The results obtained for the urinary frequencies and the daily urine volumes were designated as means±standard errors. To compare the inter-group means, a paired t-test was used.

A change in the urinary frequency during daytime or during night between before and after the intake of the investigational product was analyzed. Table 3 shows the results. Table 4 shows the results about a change in the daily urine volume between before and after the intake of the investigational product.

TABLE 3

<Change in mean urinary frequency per day (times/day)>

|  |  | Control group | Treatment group | Inter-group difference | Significant difference |
|---|---|---|---|---|---|
| Change between before and after intake | During daytime | 0.24 ± 0.21 | −0.29 ± 0.29 | −0.52 ± 0.35 | N.S. |
|  | During night | 0.17 ± 0.08 | −0.07 ± 0.09 | −0.24 ± 0.11 | P <0.05 |

TABLE 4

<Change in mean urine volume per day (mL/day)>

| Control group | Treatment group | Inter-group difference | Significant difference |
|---|---|---|---|
| Change between before and after intake 84.0 ± 100.6 | 36.9 ± 106.0 | −47.1 ± 159.1 | N.S. |

As shown in Table 3, when compared to the control group, a significant change in the mean urinary frequency during daytime was undetected in the treatment group (with a decrease of 0.52±0.53 times). By contrast, the mean urinary frequency during night was decreased significantly in the treatment group (with a decrease of 0.24±0.11 times, p<0.05).

Meanwhile, as shown in Table 4, even when compared to the control group, a significant change in the daily mean urine volume was undetected in the treatment group.

Note that there were no detected significant differences, between the control group and the treatment group, in the mean urinary frequency during daytime, the mean urinary frequency during night, and the daily mean urine volume before the intake of the investigational product.

The above results have demonstrated that rosmarinic acid exerts an effect of preventing or ameliorating nocturia and the intake thereof makes it possible to prevent or ameliorate nocturia.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2018-101411 filed in Japan on May 28, 2018, which is entirely herein incorporated by reference.

What is claimed is:

1. A method of ameliorating or treating nocturia in a subject who wants or is in need of the ameliorating or treating, comprising administering or ingesting rosmarinic acid or a salt thereof to or by the subject.

2. The method according to claim 1, wherein the rosmarinic acid or the salt thereof is in an extract of a plant belonging to the Lamiaceae family containing rosmarinic acid or a salt thereof.

3. The method according to claim 2, wherein the plant is *Perilla frutescens* Britton var. *acuta* Kudo.

4. The method according to claim 2, wherein the ratio of rosmarinic acid or a salt thereof in the extract of the plant with respect to the extract solid content in terms of rosmarinic acid content is 0.1 mass % or more and 100 mass % or less.

5. The method according to claim 1, wherein the compound is ingested by the subject.

6. The method according to claim 5, wherein the age of the subject is 20 years old or older.

7. The method according to claim 1, wherein the amount of administration or intake of the rosmarinic acid or the salt thereof in terms of rosmarinic acid content for one (1) adult (body weight 60 kg) per one (1) day is 0.1 mg or more and 40,000 mg or less.

8. The method according to claim 1, wherein the blending amount or the content of the rosmarinic acid or the salt thereof in terms of rosmarinic acid content is 0.01 mass % or more and 100 mass % or less.

9. The method according to claim 1, wherein the blending amount or the content of the rosmarinic acid or the salt thereof in terms of rosmarinic acid content is 0.001 mass % or more and 50 mass % or less.

10. The method according to claim 1, wherein the rosmarinic acid or the salt thereof is ingested or administered once a day or divisionally several times a day or during an arbitrary period and at intervals.

11. The method according to claim 1, wherein the period of ingestion or administration of the rosmarinic acid or the salt thereof is one (1) day or more.

12. The method according to claim 1, wherein the rosmarinic acid or the salt thereof is in the form of a pharmaceutical composition.

13. The method according to claim 1, wherein the rosmarinic acid or the salt thereof is in the form of a food or drink.

14. The method according to claim 13, wherein the food or drink is a food or drink for the sick, a nutritionally functional food, a food for a specified health use, or a functional food.

15. The method according to claim 1, wherein a symptom of the nocturia is that the subject wakes up from sleep to urinate.

16. The method according to claim 15, wherein a symptom of the nocturia is that the subject wakes up from sleep more than once per night to urinate.

17. The method according to claim 1, wherein amelioration or treatment of the nocturia decreases the subject's urinary desire or feeling of abdominal tension during sleep and supports the subject's sound sleep.

18. The method according to claim 1, wherein amelioration or treatment of the nocturia reduces the subject's apprehension about urination during sleep.

19. The according to claim 1, wherein the salt is at least one kind of salt selected from the group consisting of alkali metal salts and alkali earth metal salts.

\* \* \* \* \*